US00RE41391E

(19) United States
(12) Reissued Patent
Brighton

(10) Patent Number: US RE41,391 E
(45) Date of Reissued Patent: Jun. 22, 2010

(54) REGULATION OF TYPE II COLLAGEN GENE EXPRESSION USING SPECIFIC AND SELECTIVE ELECTRICAL AND ELECTROMAGNETIC SIGNALS

(75) Inventor: Carl T. Brighton, Malvern, PA (US)

(73) Assignee: The Trustees of the University of Pennsylvania, Philadelphia, PA (US)

(21) Appl. No.: 11/880,422

(22) Filed: Jul. 19, 2007

Related U.S. Patent Documents

Reissue of:
(64) Patent No.: 6,919,205
Issued: Jul. 19, 2005
Appl. No.: 10/267,708
Filed: Oct. 9, 2002

U.S. Applications:
(63) Continuation-in-part of application No. 10/257,126, filed as application No. PCT/US01/05591 on Feb. 22, 2001, now Pat. No. 7,465,566.
(60) Provisional application No. 60/184,491, filed on Feb. 23, 2000.

(51) Int. Cl.
*C12N 5/08* (2006.01)

(52) U.S. Cl. ..... 435/375; 435/377; 435/173.8; 607/65

(58) Field of Classification Search ..... None
See application file for complete search history.

(56) References Cited

U.S. PATENT DOCUMENTS

| | | | | |
|---|---|---|---|---|
| 4,430,999 | A | 2/1984 | Brighton et al. | 128/419 |
| 4,442,846 | A | 4/1984 | Brighton et al. | 128/784 |
| 4,467,808 | A | 8/1984 | Brighton et al. | 128/419 F |
| 4,467,809 | A | 8/1984 | Brighton et al. | 60/51 |
| 4,487,834 | A | 12/1984 | Brighton | 435/173 |
| 4,506,674 | A | 3/1985 | Brighton et al. | 128/419 |
| 4,509,520 | A | 4/1985 | Dugot | 128/419 |
| 4,535,775 | A | 8/1985 | Brighton et al. | 128/419 F |
| 4,549,547 | A | 10/1985 | Brighton et al. | 128/419 F |
| 4,600,010 | A | 7/1986 | Dugot | 128/419 |
| 4,683,873 | A | 8/1987 | Cadossi et al. | 128/1.5 |
| 4,998,532 | A | 3/1991 | Griffith | |
| 5,014,699 | A | 5/1991 | Pollack et al. | 128/419 |
| 5,038,797 | A | 8/1991 | Batters | 128/798 |
| 5,269,746 | A | 12/1993 | Jacobson | 600/13 |
| 5,273,033 | A | 12/1993 | Hoffman | 607/46 |
| 5,338,286 | A | 8/1994 | Abbott et al. | 600/14 |
| 5,374,283 | A | 12/1994 | Flick | 607/46 |
| 5,743,844 | A | 4/1998 | Tepper et al. | 600/14 |
| 5,968,527 | A | 10/1999 | Litovitz | 424/400 |
| 6,083,149 | A | 7/2000 | Wascher et al. | 600/9 |
| 6,132,362 | A | 10/2000 | Tepper et al. | 600/14 |
| 6,186,940 | B1 | 2/2001 | Kirschbaum | 600/12 |
| 6,261,221 | B1 | 7/2001 | Tepper et al. | 600/14 |
| 6,292,699 | B1 | 9/2001 | Simon et al. | 607/51 |
| 6,485,963 | B1 | 11/2002 | Wolf et al. | 435/298.2 |
| 6,605,089 | B1 | 8/2003 | Michelson | 606/61 |
| 6,747,004 | B1 | 6/2004 | Tabibzadeh | 514/12 |
| 6,919,205 | B2 | 7/2005 | Brighton | 435/375 |
| 6,955,642 | B1 | 10/2005 | Simon | |
| 7,022,506 | B2 | 4/2006 | Brighton et al. | |
| 7,130,692 | B2 | 10/2006 | Brighton et al. | |
| 7,158,835 | B2 | 1/2007 | Brighton et al. | |
| 7,167,753 | B2 | 1/2007 | Brighton et al. | |
| 7,215,995 | B2 | 5/2007 | Brighton et al. | |
| 7,374,916 | B2 | 5/2008 | Brighton | |
| 7,465,546 | B2 | 12/2008 | Brighton | |
| 7,465,566 | B2 * | 12/2008 | Brighton et al. | 435/173.8 |
| 2002/0038137 | A1 | 3/2002 | Stein | |
| 2002/0052634 | A1 | 5/2002 | March | 607/50 |
| 2003/0211084 | A1 | 11/2003 | Brighton et al. | 424/93.7 |
| 2005/0049640 | A1 | 3/2005 | Gurtner et al. | |
| 2005/0203591 | A1 | 9/2005 | Brighton | |
| 2006/0190043 | A1 | 8/2006 | Brighton et al. | |
| 2006/0235473 | A1 | 10/2006 | Brighton | |
| 2007/0299472 | A1 | 12/2007 | Brighton | |

FOREIGN PATENT DOCUMENTS

| | | | |
|---|---|---|---|
| EP | 0 652 028 | A1 | 5/1995 |
| EP | 1 198 580 | B1 | 5/2006 |
| RU | 2147895 | C1 | 4/2000 |
| WO | WO 00/02585 | A1 | 1/2000 |
| WO | WO 01/62336 | A1 | 8/2001 |
| WO | WO 2005/070136 | A2 | 8/2005 |

OTHER PUBLICATIONS

Heermeier. K., et al., Effects of extremely low frequency electromagnetic field (EMF) on collagen type 1 mRNA expression and extracellular matrix synthesis of human osteoblastic cells, Bioelectromagnetic, 1998, 19, 222–231.
Pezzetti, F., et al., "Effects of pulsed electromagnetic fields on human chondocytes; an in vitro study," Calcif Tissue Int., 1999, 65, 396–401.
U.S. Appl. No. 10/257,126, filed Oct. 2002, Brighton.
U.S. Appl. No. 10/255,241, filed Sep. 2002, Brighton et al.
U.S. Appl. No. 10/461,188, filed Jun. 2003, Brighton.
U.S. Appl. No. 10/585,718, filed Jul. 2006, Brighton.
Aaron, R.K., et al., "The conservative treatment of osteonecrosis of the femoral head," *Clin. Orthop.*, 1989, 249, 209–218.

*Primary Examiner*—James S Ketter
(74) *Attorney, Agent, or Firm*—Woodcock Washburn, LLP

(57) ABSTRACT

Methods and devices for the regulation of type II collagen gene expression in cartilage cells via the application of specific and selective fields generated by specific and selective electric and electromagnetic signals in the treatment of diseased or injured articular cartilage. By gene expression is meant the up regulation or down regulation of the process whereby specific portions (genes) of the human genome (DNA) are transcribed into mRNA and subsequently translated into protein. Methods and devices are provided for the targeted treatment of injured or diseased cartilage tissue that include generating specific and selective electric and electromagnetic signals that generate specific and selective fields optimized for type II collagen gene expression and exposing cartilage tissue to the specific and selective fields generated by specific and selective signals so as to regulate type II collagen gene expression in such cartilage tissue. The resulting methods and devices are useful for the targeted treatment of osteoarthritis, rheumatoid arthritis, cartilage injury, and cartilage defects.

25 Claims, 9 Drawing Sheets

Aaron, R.K., et al., "Stimulation of experimental endochondral ossification by low–energy pulsing electromagnetic fields," *K. Bone Miner. Res.*, Nov. 2, 1989, 4, 227–233.
Ala–aho, R., et al. "Targeted inhibitition of human collagenase–3 (MMP–13) expression inhibits squamous cell carcinoma growth in vivo," Oncogene, 2004–23, 5111–5123.
Bassett, C.A.L., "Low energy pulsing electromagnetic fields modify biomedical processes," *BioEssays*, 1987, 6(1), 36–42.
Bassett, C.A.L., et al. "Effects of pulsed electromagnetic fields on Steinberg ratings of femoral head osteonecrosis," *Clin. Orthop.*, Sep. 1989, 246, 172–185.
Bassett, C.A.L., et al., "Fundamental and practical aspects of therapeutic uses of pulsed electromagnetic fields (PEMSs), " *Crit. Rev. Biomed. Eng.*, 1989, 17(5), 451–529.
Bassett, C.A.L., et al., "Pulsing electromagnetic field treatment in ununited fractures and failed arthrodeses," *JAMA*, Feb. 5, 1982, 247(5), 623–628.
Binder, A., et al., "Pulsed electromagnetic field therapy of persistent rotator cuff tendonitis," *Lancet*, Mar. 31, 1984, 695–698.
Brighton, C.T., et al., "A multicenter study of the treatment of non–union with constant direct current," *J. Bone and Joint Surgery*, Jan. 1981, 62–A(1), 2–13.
Brighton, C.T., et al., "Treatment of recalcitrant non–union with a capacitively coupled electrical field," *J. Bone and Joint Surgery*, Apr. 1985, 67–A(4), 577–585.
Brighton, C.T., et al., "Treatment of castration–induced osteoporosis by a capacitively coupled electrical in rat vertebrae," *J. Bone and Joint Surgery*, Feb. 1989, 71–A(2), 228–236.
Brighton, C.T., et al., "Increased cAMP production after short–term capacitively coupled stimulation in bovine growth plate chondrocytes," *J. Orthop. Res.*, 1988, 6, 552–558.
Brighton, C.T., et al., "Treatment of denervation/disuse osteoporosis in the rat with a capacitively coupled electrical signal: effects on bone formation and bone resorption," *J. Orthop. Res.*, 1988, 6, 676–684.
Brighton, C.T., et al., "Fracture healing in the rabbit fibula when subjected to various capacitively coupled electrical fields," *J. Orthop. Res.*, 1985, 3, 331–340.
Brighton, C.T., et al., "*In vitro* bone–cell response to a capacitively coupled electrical field," *Clin. Orthop. Related Res.*, Dec. 1992, 285, 255–262.
Brighton, C.T., et al., "Signal transduction in electrically stimulated bone cells," *J. Bone Joint Surg. Am.*, 2001, 83–A(10), 1514–1523.
Brighton, C.T., et al., "Prevention and treatment of sciatic denervation disuse osteoporosis in rat tibia with capacitively coupled electrical stimulation," *Bone*, 1985, 6, 87–97.
Brighton, C.T., et al., "Treatment of nonunion of the tibia with a capacitively coupled electrical field," *J. of Trauma*, 1984, 24(2), 153–155.
Brighton, C.T., et al., "Tibial nonunion treated with direct current, capacitive coupling, or bone graft," *Clin. of Orthop. and Related Res.*, 1995, 321, 223–234.
Carter, E.L., et al., "Field distributions in vertebral bodies of the rat during electrical stimulation: a parametric study," *IEEE Trans. on Biomed. Eng.*, Mar. 1989, 36(3), 333–345.
Goodman, R., et al., "Exposure of salivary gland cells to low–frequency electromagnetic fields alters polypeptide synthesis," *Proc. Natl. Acad. Sci. USA*, Jun. 1988, 85, 3928–3932.
Goodwin, C.B., et al., "A double–blind study of capacitively coupled electrical stimulation as an adjunct to lumbar spinal fusions," *Spine*, 1999, 24(13), 1349–1356.
Grodzinsky, A.J., "Electromechanical and physicochemical properties of connective tissue," *Crit. Rev. Biomed. Engng.*, 1983, 9(2), 133–198.
Harrison, M.H.M., et al., "Use of pulsed electromagnetic fields in perthes disease: report of a pilot study," *J. Pediatr. Orthop.*, 1984, 4, 579–584.
Jiang, X., et al., "siRNA mediated inhibition of MMP–1 reduces invasive potential of a human chondrosarcoma cell line," J. of Cellular Physiology, 2005, 202, 723–730.
Jones, D.B., et al., "PEMF effects on differentiation and division in mirine melanoma cells are mediated indirectly through cAMP," *Trans. BRAGS 6*, 1986, 51.
Lorich, D.G., et al., "Biochemical pathway mediating the response on bone cells to capacitive coupling," *Clin. Orthop. and Related Res.*, 1998, 350, 246–256.
Massardo, L., et al., "Osteoarthritis of the knee joint: an eight year prospective study," *Ann Rheum Dis.*, 1989, 48, 893–897.
Mooney, V., "A randomized double–blind prospective study of the efficacy of pulsed electromagnetic fields for inter body lumbar fusions," *Spine*, 1990, 15(7), 708–712.
Norton, L.A., et al., "Pulsed electromagnetic fields alter phenotypic expression in chondroblasts in tissue culture,", *J. Orthop. Res.*, 1988, 6, 685–689.
Pienkowski, D., et al., "Low–power electromagnetic stimulation of osteotomized rabbit fibuiae," *J. of Bone & Joint Surgery*, 1994, 76–A(4), 489–501.
Rodan, G.A., et al., "DNA synthesis in cartilage cells is stimulated by oscillating electric fields," *Science*, Feb. 10, 1978, 199, 690–692.
Ryaby, J.T., et al., "Pulsing electromagnetic fields affect the phosphorylation and expression of oncogene proteins," *Trans. BRAGS 6*, 1986, p. 78.
Ryaby, J.T., et al., "The effect of electromagnetic fields on protein phosphorylation and synthesis in murine melanoma cells," *BRAGS*, p. 32, 1986.
Wang, W. et al., "The increased level of PDGF—A contributes to increased proliferation induced by mechanical stimulation in osteoblastic cells," *Biochem Biophys. Res. Commun.*, Oct. 1997, 43(2), 339–346.
Wang, W., et al., "The increased level of PDGF–A constributes to the increased proliferation induced by mechanical stimulation in osteoblastic cells," *Biochem. And Molecular Biol. International*, Oct. 1997, 43(2), 339–346.
Wang, W., et al., "Up–regulation of chondrocyte matrix genes and products by electric fields," *Clin. Orthopaedics& Related Res.*, 2004, 427S, S163–S173.
Zhuang, H., et al., "Mechanical strain–induced proliferation of osteoblastic cells parallels increased TGF–β1 mRNA," *Biochem. Biophys. Res. Commum.*, 1996, 229, 449–453.
Zhuang, H., et al., "Electrical stimulation induces the level of TGF–β1 mRNA in osteoblastic cells by a mechanism involving calcium/calmodulin pathway," *Biochem. Biophys. Res. Commun.*, 1997, 237, 225–229.
The PCT International Search Report dated Aug. 5, 2004 (PCT/US03/3173).*

* cited by examiner

REGULATION OF TYPE II COLLAGEN GENE EXPRESSION USING SPECIFIC AND SELECTIVE ELECTRICAL AND ELECTROMAGNETIC SIGNALS

Matter enclosed in heavy brackets [ ] appears in the original patent but forms no part of this reissue specification; matter printed in italics indicates the additions made by reissue.

CROSS-REFERENCE TO RELATED APPLICATIONS

The present patent application is a continuation-in-part patent application of U.S. patent application Ser. No. 10/257,126, filed Oct. 8, 2002, which is the U.S. national phase patent application of PCT/US01/05991, filed Feb. 22, 2001, which, in turn, claims the benefit of the filing date of U.S. Provisional Patent Application Ser. No. 60/184,491, filed Feb. 23, 2000.

FIELD OF THE INVENTION

The present invention is directed to a method of regulating type II collagen gene expression in cartilage cells via the application of specific and selective fields generated by specific and selective electric and electromagnetic signals for the treatment of injured or diseased articular cartilage, as well as a device for generating such signals.

BACKGROUND OF THE INVENTION

The bioelectrical interactions and activity believed to be present in a variety of biological tissues and cells are one of the least understood of the physiological processes. However, there has recently been much research into these interactions and activity regarding the growth and repair of certain tissues and cells. In particular, there has been much research into stimulation by electric and electromagnetic fields and its effect on the growth and repair of bone and cartilage. Researchers believe that such research might be useful in the development of new treatments for a variety of medical problems.

Osteoarthritis, also known as degenerative joint disease, is characterized by degeneration of articular cartilage as well as proliferation and remodeling of subchondral bone. The usual symptoms are stiffness, limitation of motion, and pain. Osteoarthritis is the most common form of arthritis, and prevalence rates increase markedly with age. It has been shown than elderly patients with self-reported osteoarthritis visit doctors twice as frequently as their unaffected peers. Such patients also experience more days of restricted activity and bed confinement compared to others in their age group. In one study, the majority of symptomatic patients became significantly disabled during an 8-year follow-up period. Massardo et al., Ann Rheum Dis 48: 893–7 (1989).

Nonsteroidal anti-inflammatory drugs (NSAIDs) remain the primary treatment modality for osteoarthritis. It is unknown whether the efficacy of NSAIDs is dependent upon their analgesic or anti-inflammatory properties or the slowing of degenerative processes in the cartilage. There is also a concern that NSAIDs may be deleterious to patients. For example, NSAIDs have well known toxic effects in the stomach, gastrointestinal tract, liver and kidney. However, aspirin inhibits proteoglycan synthesis and normal cartilaginous repair processes in animals. One study in humans suggested that indomethacin might accelerate breakdown of hip cartilage. All adverse effects appear more commonly in the elderly—the very population most susceptible to osteoarthritis.

In the disease commonly known as osteoporosis, bone demineralizes and becomes abnormally rarefied. Bone comprises an organic component of cells and matrix as well as an inorganic or mineral component. The cells and matrix comprise a framework of collagenous fibers that is impregnated with the mineral component of calcium phosphate (85%) and calcium carbonate (10%) that imparts rigidity to the bone. While osteoporosis is generally thought as afflicting the elderly, certain types of osteoporosis may affect persons of all ages whose bones are not subject to functional stress. In such cases, patients may experience a significant loss of cortical and cancellous bone during prolonged periods of immobilization. Elderly patients are known to experience bone loss due to disuse when immobilized after fracture of a bone, which may ultimately lead to a secondary fracture in an already osteoporotic skeleton. Diminished bone density may lead to vertebrae collapse, fractures of hips, lower arms, wrists, ankles as well as incapacitating pains. Alternative nonsurgical therapies for such diseases are needed.

Pulsed electromagnetic fields (PEMF) and capacitive coupling (CC) have been used widely to treat nonhealing fractures and related problems in bone healing since approval by the Food and Drug Administration in 1979. The original basis for the trial of this form of therapy was the observation that physical stress on bone causes the appearance of tiny electric currents that, along with mechanical strain, were thought to be the mechanisms underlying transduction of the physical stresses into a signal that promotes bone formation. Along with direct electric field stimulation that was successful in the treatment of nonunion, noninvasive technologies using PEMF and capacitive coupling (where the electrodes are placed on the skin in the treatment zone) were also found to be effective. Pulsed electromagnetic fields generate small induced currents (Faraday currents) in the highly conductive extracellular fluid, while capacitive coupling directly causes currents in the tissues; both PEMFs and CC thereby mimic endogeneous electrical currents.

The endogeneous electrical currents, originally thought to be due to phenomena occurring at the surface of crystals in the bone, have been shown to be due primarily to movement of fluid containing electrolytes in channels of the bone containing organic constituents with fixed negative charges, generating what are called "streaming potentials." Studies of electrical phenomena in cartilage have demonstrated a mechanical-electrical transduction mechanism that resembles those described in bone, appearing when cartilage is mechanically compressed, causing movement of fluid and electrolytes over the surface of fixed negative charges in the proteoglycans and collagen in the cartilage matrix. These streaming potentials apparently serve a purpose in cartilage similar to that in bone, and, along with mechanical strain, lead to signal transduction that is capable of stimulating chondrocyte synthesis of matrix components.

The main application of direct current, capacitive coupling, and PEMFs has been in orthopedics in healing of nonunion bone fractures (Brighton et al., J. Bone and Joint Surgery, 63: 2–13, 1981; Brighton and Pollack, J. Bone and Joint Surgery, 67: 577–585, 1985; Bassett et al., Crit. Rev. Biomed. Eng., 17: 451–529(1989); Bassett et al., J AMA 247: 623–8 (1982). Clinical responses have been reported in avascular necrosis of hips in adults and Legg-Perthes's disease in children. Bassett et al., Clin Orthop 246: 172–6 (1989); Aaron et al., Clin Orthop 249: 209–18 (1989); Harrison et al,J. Pediatr Orthop 4: 579–84 (1984). It has also been shown that PEMFs (Mooney, Spine, 15: 708–712, 1990) and capacitive coupling (Goodwin, Brighton et al., Spine, 24: 1349–1356, 1999) can significantly increase the success rate of lumbar fusions. There are also reports of augmentation of peripheral nerve regeneration and function and promotion of angiogenesis. Bassett, Bioassays 6: 36–42 (1987). Patients with persistent rotator cufftendiniits refractory to steroid injection and other conventional measures, showed significant benefit compared with placebo treated patients. Binder et al., Lancet 695–8 (1984). Finally, Brighton et al. have shown in rats the ability of an appropriate capacitive coupling electric field to both prevent and reverse vertebral osteoporosis in the lumbar spine (Brighton et al., J. Orthop. Res. 6: 676–684, 1988; Brighton et al., J. Bone and Joint Surgery, 71: 228–236, 1989).

More recently, research in this area has focused on the effects stimulation has on tissues and cells. For example, it has been conjectured that direct currents do not penetrate cellular membranes and that control is achieved via extracellular matrix differentiation. Grodzinsky, Crit. Rev. Biomed. Engng 9:133 (1983). In contrast to direct currents, it has been reported that PEMFs can penetrate cell membranes and either stimulate them or directly affect intracellular organelles. An examination of the effect of PEMFs on extracellular matrices and in vivo endochondral ossification found increased synthesis of cartilage molecules and maturation of bone trabeculae. Aaron et al., J. Bone Miner. Res. 4: 227–233 (1989). More recently, Lorich, Brighton et al. reported (Clin Orthop and Related Research 350: 246–256, 1998) that signal transduction of a capacitively coupled electric signal is via voltage gated calcium channels, leading to an increase in cytosolic calcium with a subsequent increase in activated (cytoskeletal) calmodulin.

Much research has been directed at studying tissue culture in order to understand the mechanisms of response. In one study, it was found that electric fields increased [$^3$H] thymidine incorporation into the DNA of chondrocytes, supporting the notion that Na and $Ca^{2+}$ fluxes generated by electrical stimulation trigger DNA synthesis. Rodan et al., Science 199: 690–692 (1978). Studies have found changes in the second messenger, cAMP, and cytoskeletal rearrangements due to electrical perturbations. Ryaby et al., Trans. BRAGS 6: (1986); Jones et al., Trans. BRAGS 6:51 (1986); Brighton and Townsend, J. Orthop. Res. 6: 552–558, 1988. Other studies have found effects on glycosaminoglycan, sulphation, hyaluronic acid, lysozyme activity and polypeptide sequences. Norton et al., J. Orthop. Res. 6: 685–689 (1988); Goodman et al., Proc. Natn. Acad. Sci. USA 85: 3928–3932 (1988).

It was reported in 1996 by the present inventor that a cyclic biaxial 0.17% mechanical strain produces a significant increase in TGF-$\beta_1$ mRNA in cultured MC3T3-E1 bone cells. Brighton et al., Biochem. Biophys. Res. Commun. 229: 449–453 (1996). Several significant studies followed in 1997. In one study it was reported that the same cyclic biaxial 0.17% mechanical strain produced a significant increase in PDGF-A mRNA in similar bone cells. Brighton et al., Biochem. Biophys. Res. Commun. 43: 339–346 (1997). It was also reported that a 60 kHz capacitively coupled electric field of 20 mV/cm produced a significant increase in TGF-$\beta_1$ in similar bone cells. Brighton et al., Biochem. Biophys. Res. Commun. 237: 225–229 (1997). However, the effect such a field would have on other genes has not been reported in the literature.

In the above-referenced parent patent application, entitled "Regulation of Genes Via Application of Specific and Selective Electrical and Electromagnetic Signals," methods were disclosed for determining the specific and selective electrical and electromagnetic signals for use in creating specific and selective fields for regulating target genes of diseased or injured tissues. The present invention builds upon the technique described therein by describing the method of regulating one targeted gene expression, namely, type II collagen gene expression, through application of a specific and selective field generated by a specific and selective electrical and electromagnetic signal, for the treatment of cartilage disease (arthritis), cartilage injury, and cartilage defects.

SUMMARY OF THE INVENTION

The present invention relates to regulating the type II collagen gene expression in cartilage cells via the application of specific and selective fields generated by specific and selective electric and/or electromagnetic signals. By performing dose-response curves on the electric field duration, amplitude, frequency, and duty cycle, the optimal signal for up-regulating type II collagen mRNA in articular cartilage chondrocytes was discovered. The optimal signal generated a capacitively coupled electric field with an amplitude of 20 mV/cm, a duration of 30 minutes, a duty cycle of 8.3% (1 minute ON, 11 minutes OFF, 30 cycles), a frequency of 60 kHz, and a sine wave configuration. In particular, the present invention relates to up-regulating type II collagen gene expression in cartilage cells via the application of fields generated by such signals.

In a preferred embodiment of the invention, methods are provided to specifically and selectively up-regulate the gene expression of type II collagen mRNA with capacitively coupled electric fields, electromagnetic fields, or combined fields. Osteoarthritis, rheumatoid arthritis, cartilage injury, cartilage defects, and the like are treated with a capacitively coupled electric field of about 20 mV/cm with an electric field duration of about 30 minutes, a frequency of about 60 kHz, a duty cycle of about 8.3%, and a sine wave configuration that causes the expression of type II collagen mRNA to be up-regulated. In accordance with the method of the invention, a "specific and selective" signal is a signal that has predetermined characteristics of amplitude, duration, duty-cycle, frequency, and waveform that up-regulates the expression of the type II collagen gene (specificity). This allows one to choose different signals to up-regulate type II collagen gene expressions in order to achieve a given biological or therapeutic response (selectivity). The invention further relates to devices employing the methods described herein to generate specific and selective signals that create specific and selective fields to up-regulate the expression of the type II collagen gene.

In related aspects, the present invention relates to methods and devices for the treatment of osteoarthritis, rheumatoid arthritis, cartilage injury, and cartilage defects. The method of the invention also includes the methodology for determining the "specific and selective" signal for the type II collagen gene by methodically varying the duration of a starting signal known to increase or suspected to increase cellular production of type II collagen. After selecting the optimal duration, the amplitude of the signal is varied for the optimal duration of time as determined by the gene expression of type II collagen. The duty cycle, frequency, and waveform are varied methodically while keeping the other signal characteristics constant. This process is repeated until the optimal signal is determined that produces the greatest increase in the expression of type II collagen.

Those skilled in the art will appreciate that type II collagen gene expression is functionally complementary or synergistic to aggrecan gene expression in cartilage cells exposed to various electrical and electromagnetic signals. Specific and selective signals for regulating aggrecan gene expression are described in copending U.S. patent application Ser. No. 10/255,241, also to the present inventor. These and other aspects of the present invention will be elucidated in the following detailed description of the invention.

BRIEF DESCRIPTION OF THE DRAWINGS

The present invention will be apparent from the following detailed description of the invention taken in conjunction with the accompanying drawings, of which.

DETAILED DESCRIPTION OF PREFERRED EMBODIMENTS OF THE INVENTION

Figure 1:
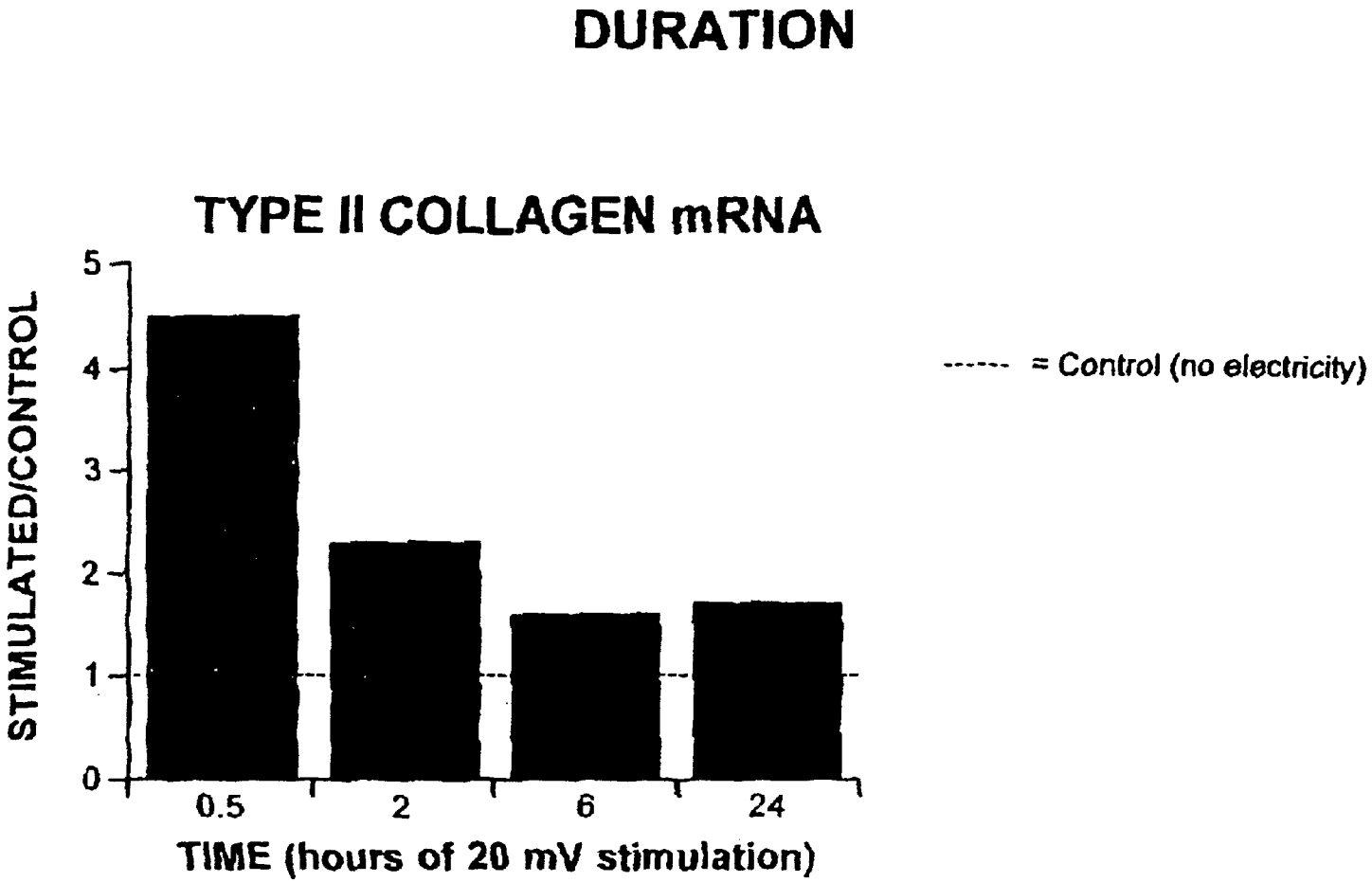
FIG. 1 is a graphic representation of type II collagen mRNA expression when articular cartilage chondrocytes are exposed to a 20 mV/cm capacitively coupled electric field for various time durations. As indicated, the optimum type II collagen mRNA production occurred with a signal of 30 minutes duration.

The invention will be described in detail below with reference to FIGS. 1–9. Those skilled in the art will appreciate that the description given herein with respect to those figures is for exemplary purposes only and is not intended in any way to limit the scope of the invention. All questions regarding the scope of the invention may be resolved by referring to the appended claims.

The present invention is based on the discovery that the expression of certain genes can be regulated by the application of specific and selective fields generated by specific and selective electric and/or electromagnetic signals. In other words, it has been discovered by the present inventor that there is a specific and selective electric and/or electromagnetic signal that generates a specific and selective field for regulating each gene in bone, cartilage and other tissue cells and that these fields are capable of specifically and selectively regulating the genes in such cells. In particular, gene expression governing the growth, maintenance, repair, and degeneration or deterioration of tissues or cells can be regulated in accordance with the invention via the application of specific and selective fields generated by specific and selective electric and/or electromagnetic signals so as to produce a salutary clinical effect. Such discoveries are useful in the development of treatment methods that target certain medical conditions including bone fractures and defects, osteoarthritis, osteoporosis, cancer and other diseases, as well as for developing devices employing such methods.

In particular, the present invention demonstrates that the expression of type II collagen may be significantly up-regulated to increase the production of collagen in articular cartilage. Type II collagen, along with aggrecan, are the main constituents of articular cartilage that are compromised and/or degraded early in the course of arthritis. The present invention clearly shows that the optimal electric field described herein can significantly up-regulate type II collagen mRNA and, hence, increase type II collagen synthesis, even in the presence of IL-1β. Those skilled in the art will also appreciate that an appropriate electric field, as described herein with capacitive coupling but equally effective with any and all field application techniques, can be used to treat arthritis (both osteoarthritis and rheumatoid arthritis), cartilage injury, and cartilage defects.

As used herein, the phrase "signal" is used to refer to a variety of signals including mechanical signals, ultrasound signals, electromagnetic signals and electric signals output by a device. It is to be understood that the term "field" as used herein refers to an electrical field within targeted tissue, whether it is a combined field or a pulsed electromagnetic field or generated by direct current, capacitive coupling or inductive coupling.

The phrase "remote" is used to mean acting, acted on or controlled from a distance. "Remote" regulation refers to controlling the expression of a gene from a distance. To provide "remotely" refers to providing from a distance. For example, providing a specific and selective signal from a remote source can refer to providing the signal from a source at a distance to tissue or a cell or from a source outside of or external to the body.

The phrase "specific and selective" signal means a signal that produces a specific and selective electric field that has predetermined characteristics of amplitude, duration, duty-cycle, frequency, and waveform that up-regulate or down-regulate a targeted gene or targeted functionally complementary genes (specificity). This allows one to choose different "specific and selective" signals to up-regulate or down-regulate various gene expressions in order to achieve a given biological or therapeutic response (selectivity).

The term "regulate" means to control gene expression. Regulate is understood to include both up-regulate and down-regulate. Up-regulate means to increase expression of a gene, while down-regulate means to inhibit or prevent expression of a gene.

"Functionally complementary" refers to two or more genes whose expressions are complementary or synergistic in a given cell or tissue.

"Tissues" refers to an aggregate of cells together with their extracellular substances that form one of the structural materials of a patient. As used herein, the term "tissue" is intended to include muscle and organ tissue as well as bone or cartilage tissue. Also, the term "tissue" as used herein may also refer to an individual cell.

"Patient" refers to an animal, preferably a mammal, more preferably a human.

The present invention provides treatment methods and devices that target certain tissues, cells or diseases. In particular, the gene expression associated with the repair process in injured or diseased tissues or cells can be regulated by the application of specific and selective fields generated by electric signals that are specific and selective for the genes to be regulated in the target tissues or cells. Gene expression can be up-regulated or down-regulated by the application of signals that are specific and selective for each gene or each set of complementary genes so as to produce a beneficial clinical effect. For example, a particular specific and selective signal may create a specific and selective electric field that up-regulates a certain desirable gene expression, while the same or another particular specific and selective signal may create a specific and selective electric field that down-regulates a certain undesirable gene expression. A certain gene may be up-regulated by a specific and selective field generated by one particular specific and selective signal and down-regulated by a specific and selective field generated by another specific and selective signal. Those skilled in the art will understand that certain diseased or injured tissues can be targeted for treatment by regulating those genes governing the growth, maintenance, repair, and degeneration or deterioration of the tissues.

The methods and devices of the present invention are based on identifying those signals that generate fields that are specific and selective for the gene expression associated with certain targeted diseased or injured tissue. For example, electricity in its various forms (e.g., capacitive coupling, inductive coupling, combined fields) can specifically and selectively regulate gene expression in targeted tissues or cells in a patient's body by varying the frequency, amplitude, waveform or duty cycle of the applied specific and selective field for each selected gene. The duration of time exposed to electricity can also influence the capability of electricity to specifically and selectivity regulate gene expression in targeted tissues or cells in a patient's body. Specific and selective signals may generate specific and selective electric fields for application to each gene systematically until the proper combination of frequency, amplitude, waveform, duty cycle, and duration is found that provides the desired effect on gene expression.

It is to be understood that a variety of diseased or injured tissues or disease states can be targeted for treatment because the specificity and selectivity of an electric field for a certain gene expression can be influenced by several factors. In particular, an electrical field of appropriate frequency, amplitude, waveform and/or duty cycle can be specific and selective for the expression of certain genes and thus provide for targeted treatments. Temporal factors (e.g., duration of time exposed to the electrical field) can also influence the specificity and selectivity of an electric field for a particular gene expression. The regulation of gene expression may be more effective (or made possible) via the application of a specific and selective electrical field for a particular duration of time. Therefore, those skilled in the art will understand that the present invention provides for varying the frequency, amplitude, waveform, duty cycle and/or duration of application of an electric field until the electric field is found to be specific and selective for certain gene expressions in order to provide for treatments targeting a variety of diseased or injured tissue or diseases.

Thus, the present invention can provide for targeted treatments because it is possible to regulate expression of certain genes associated with a particular diseased or injured tissue via the application of specific and selective fields generated by specific and selective signals of appropriate frequency, amplitude, waveform and/or duty cycle for an appropriate duration of time. The specificity and selectivity of a signal generating a specific and selective electrical field may thus be influenced so as to regulate the expression of certain genes in order to target certain diseased or injured tissue or disease states for treatment. In particular, the present invention provides for the targeted treatment of osteoarthritis, rheumatoid arthritis, cartilage injury, and cartilage defects.

The present invention also provides a device that includes a source of at least one signal specific and selective for type II collagen gene expression. The devices of the present invention can provide for the production of such signals for application to cartilage cells by at least one electrode adapted to apply the specific and selective field generated by the specific and selective signal. In particular, the optimal field described herein can be applied to any joint via appropriate surface electrodes, two or more, in pairs or in strips, incorporated in garments, braces, wraps or casts, and delivered by means of capacitive coupling, inductive coupling (electromagnetic fields), or combined fields.

Figure 9:
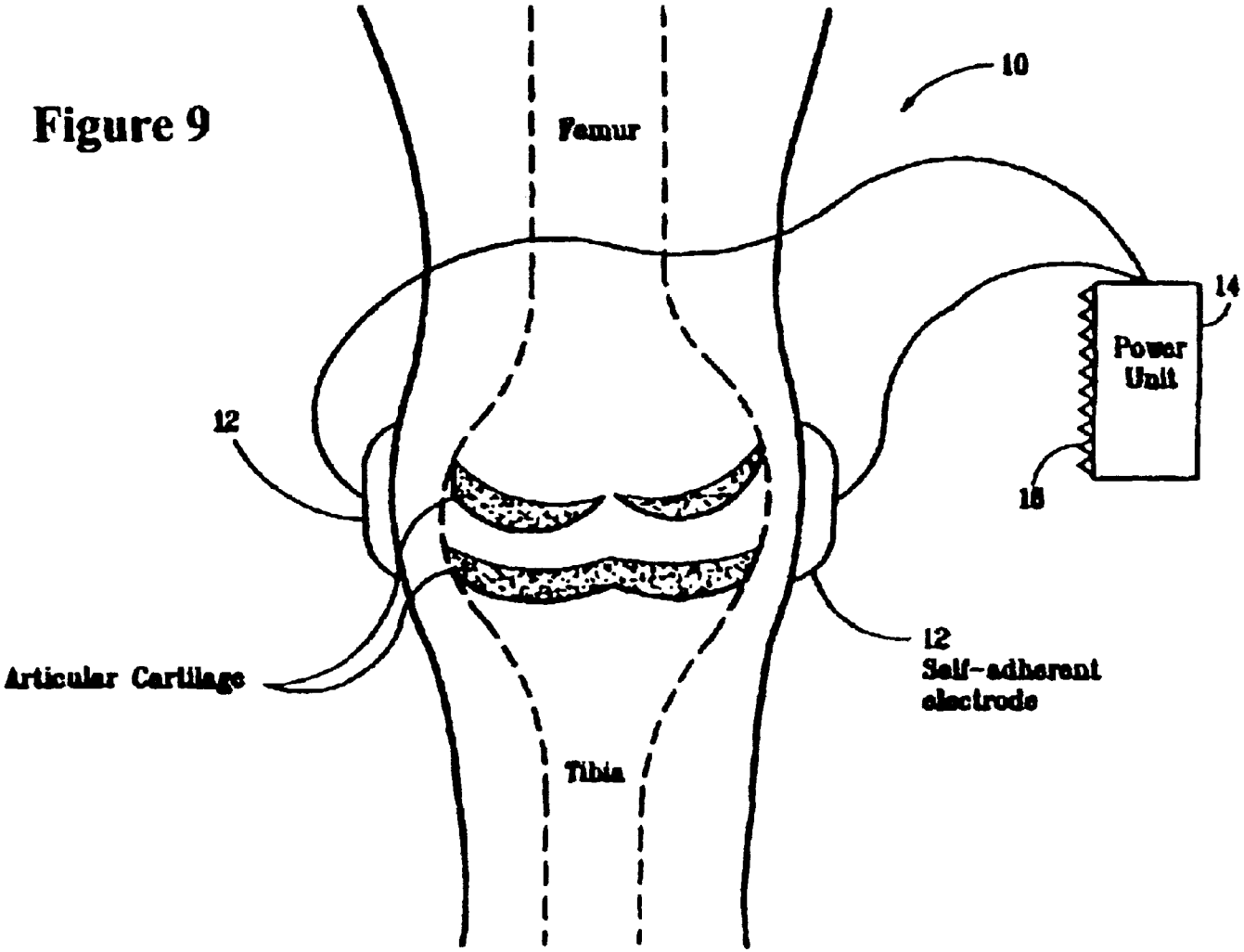
FIG. 9 illustrates a device 10 in accordance with the present invention that is used to treat a patient with osteoarthritis of the knee.

The device of the present invention is capable of applying a specific and selective field generated by specific and selective signals directly to diseased or injured tissue and/or to the skin of a patient. The device of the present invention may also provide for the remote application of specific and selective fields (e.g., application of a field at a distance from diseased or injured tissue), although it will be appreciated that capacitively coupled devices must touch the subject's skin. The device of the present invention may include means for attaching the electrodes to the body of a patient in the vicinity of injured or diseased tissue. For example, self-adherent conductive electrodes may be attached to the skin of the patient on both sides of a knee joint afflicted with osteoarthritis as shown in FIG. 9. As also shown in FIG. 9, the device 10 of the present invention may include self-adherent electrodes 12 for attaching the device 10 to the body of a patient. For example, the device 10 of the present invention may include electrodes 12 attached to a power unit 14 that has a VELCRO® patch 16 on the reverse side such that the power unit 14 can be attached to a VELCRO® strap (not shown) fitted around the calf, thigh or waist of the patient.

The device 10 of the present invention can be employed in a variety of ways. The device 10 may be portable or may be temporarily or permanently attached to a patient's body. The device 10 of the present invention is preferably non-invasive. For example, the device 10 of the present invention may be applied to the skin of a patient by application of electrodes adapted for contact with the skin of a patient for the application of specific and selective fields generated by the predetermined specific and selective signals. Such signals may also be applied via coils in which time varying currents flow, thus producing specific and selective electromagnetic fields that penetrate the tissue. The device 10 of the present invention may also be capable of implantation in a patient, including implantation under the skin of a patient.

The example below will illustrate that the method of the present invention may provide for cartilage growth and repair. Cartilage growth and repair can be stimulated via signals specific and selective for the regulation of expression of type II collagen in cartilage cells so as to stimulate articular cartilage repair in osteoarthritis patients. In particular, the methods of the present invention can provide for the up-regulation of type II collagen genes that repair cartilage. A variety of cartilage cells can be targeted by the methods of the present invention including articular chondrocytes and including articular cartilage, hyaline cartilage, and growth plate cartilage.

The example below further illustrates that the method of the present invention provides for the regulation of gene expression in articular chondrocytes. For example, in the example below, fetal articular chondrocytes have been exposed to a capacitively coupled 60 kHz electrical field of 20 mV/cm for 0.5, 2.0, 6.0 and 24.0 hours. A statistically significant incorporation of $^{35}SO_4$/ug DNA (indicating significant proteoglycan synthesis) was found after only 0.5 hours of stimulation. An identical experiment was repeated and the levels of type II collagen mRNA, the messenger for the major cartilage proteoglycan, monitored. After only 0.5 hours of electrical stimulation there was a significant increase in type II collagen mRNA. Accordingly, temporal factors may influence the specificity and selectivity of a signal that generates specific and selective electric fields for regulating gene expression in articular chondrocytes.

Those skilled in the art will understand that a variety of other cartilage diseases and injuries may be targeted for treatment via the method of the present invention.

Those skilled in the art will further understand that the devices of the present invention can be provided in a variety of forms including a capacitively coupled power unit with programmed multiple switchable specific and selective signals for application to one pair or to multiple pairs of electrodes, electromagnetic coils attached to a power unit with switchable multiple specific and selective signals, and an ultrasound stimulator with a power supply for generating specific and selective signals. Generally speaking, device preference is based on patient acceptance and patient compliance. The smallest and most portable unit available in the art at the present time is a capacitive coupling unit; however, patients with extremely sensitive skin may prefer to use inductive coupling units. On the other hand, ultrasound units require the most patient cooperation but may be desirable for use by certain patients.

EXAMPLE

The invention is demonstrated in the following example, which is for purposes of illustration and is not intended to limit the scope of the present invention.

Materials and Methods

Chondrocyte cultures were prepared from fetal bovine articular cartilage. Chondrocytes ($5\times10^5$ cells/cm$^2$) were plated onto specially modified Cooper dishes. The cells were grown to seven days with the medium changed just prior to beginning of the experimental condition. The experimental cell cultures throughout these studies were subjected to a capacitively coupled 60 kHz sine wave signal electric field with an output of 44.81 volts peak to peak. This produced a calculated-field strength in the culture medium in the dishes of 20 mV/cm with a current density of 300 μA/cm$^2$. Control cell culture dishes were identical to that of the stimulated dishes except that the electrodes were not connected to a function generator.

Total RNA was isolated using TRIzol, according to the manufacturer's instructions, and reversed transcription using SuperScript II reverse trnascriptase was performed. Oligonucletoide primers to be used in the competitive PCR technique were selected from published cDNA sequences. Quantitative analysis of PCR products was performed using ScionImage software.

Figure 2:
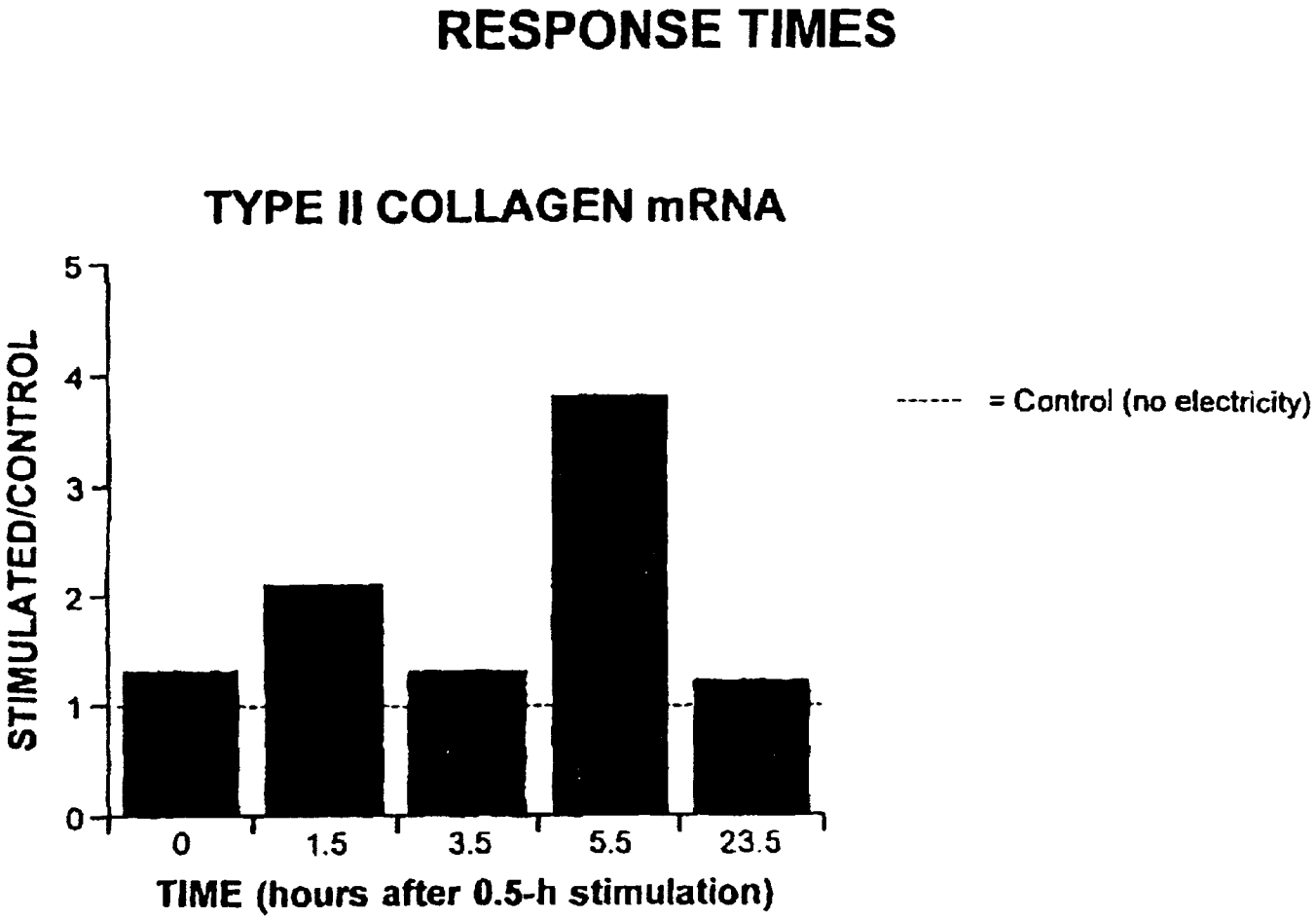
FIG. 2 is a graphic representation of type II collagen mRNA expression when articular cartilage chondrocytes are exposed to a 20 mV/cm capacitively coupled field for 30 minutes. The amount of type II collagen mRNA produced after various response times—as compared to that of controls (no electricity)—is shown. As also shown, the optimum type II collagen mRNA production occurred 5.5 hours after the electrical stimulation ceased.
Figure 5:
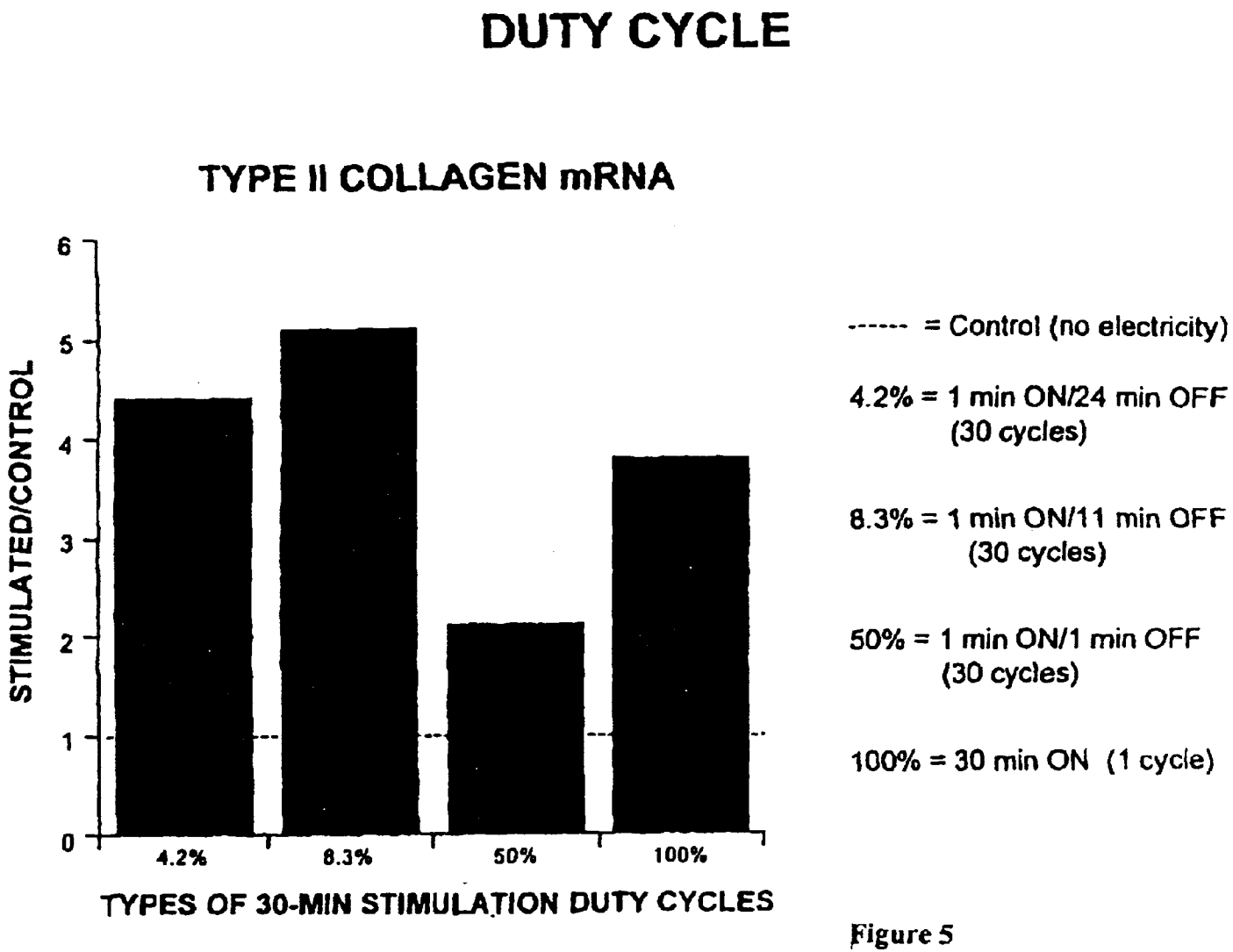
FIG. 5 is a graphic representation of type II collagen mRNA expression when articular cartilage chondrocytes are exposed to a capacitively coupled electric field of various duty cycles with a duration of 30 minutes ON time at 20 mV/cm electric field amplitude and harvested 5.5 hours after cessation of the electrical signal. As indicated, the optimum duty cycle was found to be 8.3% (1 minute ON, 11 minutes OFF, 30 cycles).

The optimal signal for the desired gene regulation was found systematically as follows. An electrical signal known to increase (or even just suspected to increase) cellular production of a given protein is taken as the starting signal for determining the specific signal for generating the specific and selective field of the gene expression (mRNA) of that protein. A dose-response curve is first performed by varying the duration of the signal while holding all the other signal characteristics constant (amplitude, duty-cycle, frequency, and waveform) (FIG. 1). This determines the optimal duration of the starting signal for the gene expression of that protein. A second dose-response curve is performed by varying the field amplitude (FIG. 3) for the optimal duration of time (FIG. 2). This determines the optimal field amplitude for the optimal duration of time as determined by the gene expression of the protein of interest. A third dose-response curve is then performed, this time varying the duty-cycle from 100% (constant) to 5% or less while holding the optimal amplitude and other signal characteristics constant (FIG. 5). A dose-response is repeated a fourth time (varying frequency) (FIG. 6) keeping the other signal characteristics constant. Though not shown, the dose response may be repeated a fifth time (varying waveform) each time keeping the other signal characteristics constant. By this method an optimal signal is determined for producing the greatest increase in the gene expression of the protein of interest.

Gene expression may be determined by any method known in the art, such as reverse transcription PCR and Northern analysis, and protein expression may be determined by spectrophotometric, fluorometric, etc. immunoassays, and the like.

Type II Collagen Production by Articular Chondrocytes

Articular chondrocytes were exposed to a capacitively coupled electric field of 20 mV/cm at 60 kHz. The results are illustrated in FIGS. 1–8.

FIG. 1 is a graphic representation of type II collagen mRNA expression when articular cartilage chondrocytes (attomole per μl) are exposed at a 20 mV/cm capacitively coupled electric field for various time durations (0.5, 2, 6, and 24 hours). As indicated, the optimum type II collagen mRNA production occurred with a signal of 30 minutes duration.

FIG. 2 is a graphic representation of type II collagen mRNA expression when articular cartilage chondrocytes (attomole per μl) are exposed to a 20 mV/cm capacitively coupled field for 30 minutes. The amount of type II collagen mRNA produced after various response times—as compared to that of controls (no electricity)—is shown. As also shown, the optimum type II collagen mRNA production occurred 5.5 hours after the electrical stimulation ceased.

Figure 3:
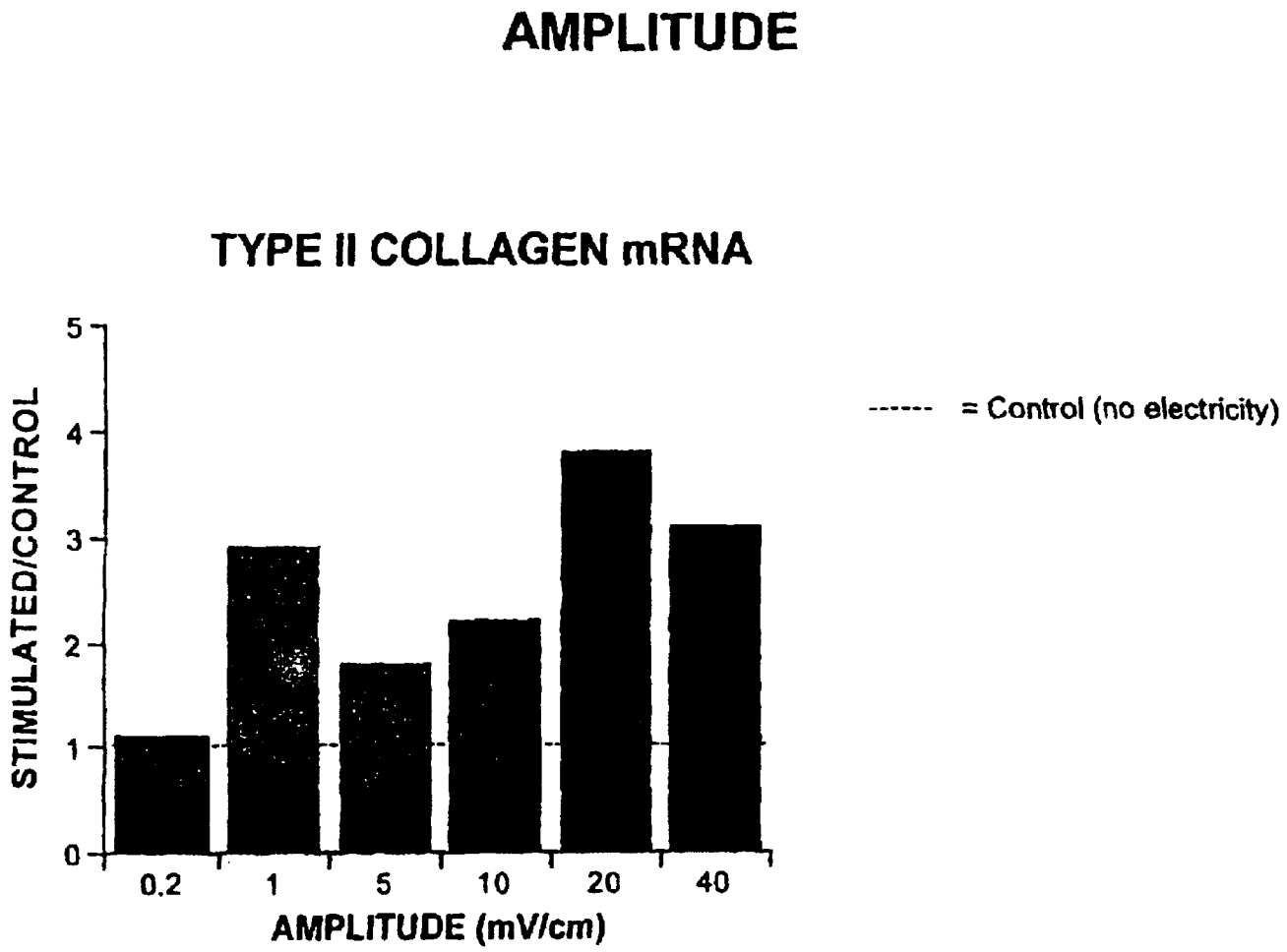
FIG. 3 is a graphic representation of type II collagen mRNA expression when articular cartilage chondrocytes are exposed to various amplitudes of a capacitively coupled electric field for 30 minutes' duration and harvested 5.5 hours after the electrical stimulation ceased. As indicated, the optimum production of type II collagen mRNA occurred with a signal producing an electric field amplitude of 20 mV/cm.

FIG. 3 is a graphic representation of type II collagen mRNA expression when articular cartilage chondrocytes are exposed to various amplitudes of a capacitively coupled electric field for 30 minutes' duration and harvested 5.5 hours after the electrical stimulation ceased. As indicated, the optimum production of type II collagen mRNA occurred with a signal producing an electric field amplitude of 20 mV/cm. By comparison, the optimal amplitude established for aggrecan mRNA has been found by the present inventor to be 10–20 mV/cm.

Figure 4:
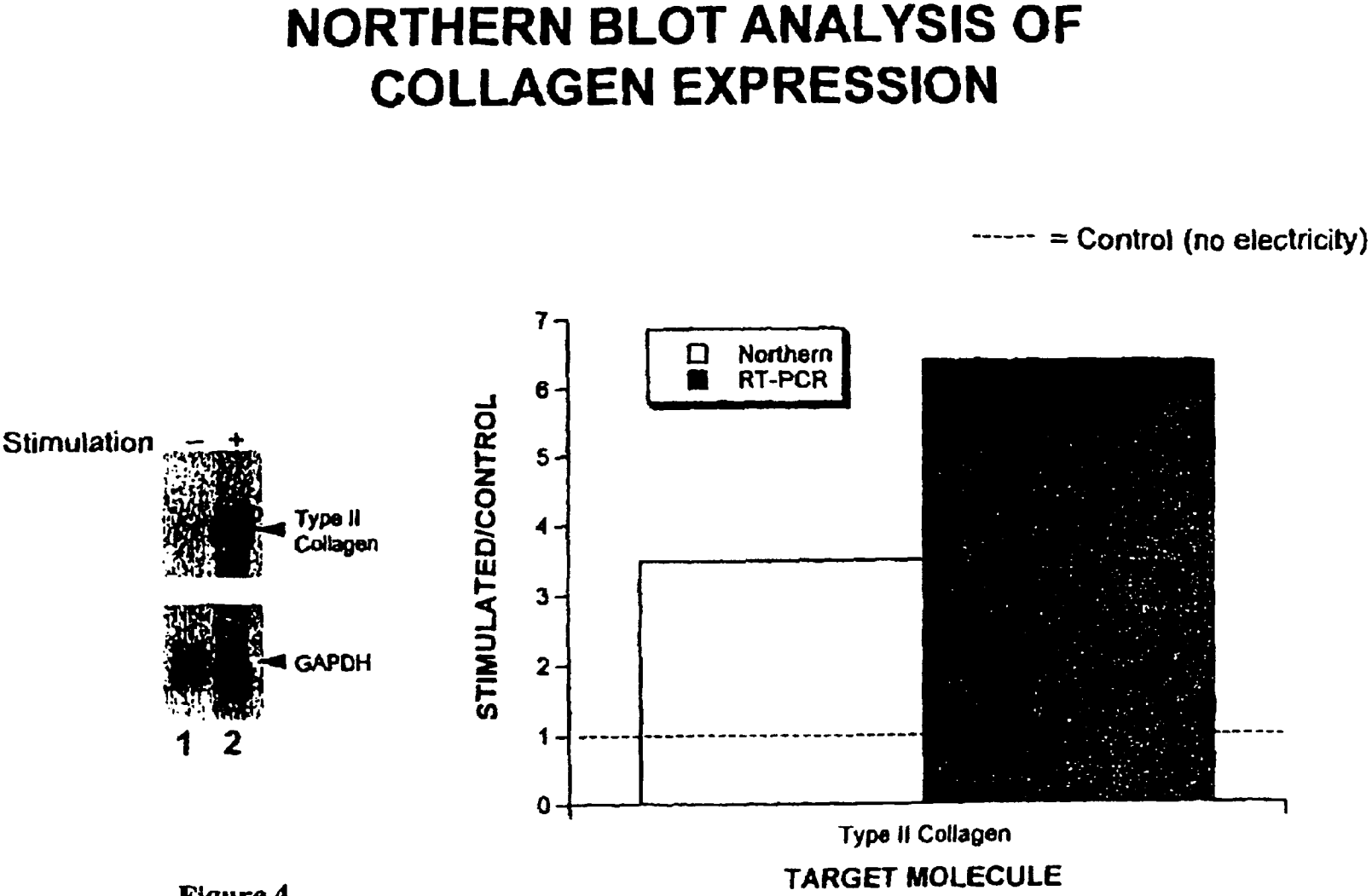
FIG. 4 is a graphic representation of Northern blot analysis of type II collagen expression (white bar) and type II collagen mRNA expression (shaded bar) when articular cartilage chondrocytes are exposed to 20 mV/cm capacitively coupled electric field for 30 minutes' duration and harvested 5.5 hours after cessation of the electrical signal. As indicated, the Northern blot analysis of the type II collagen mRNA is 3.5-fold greater than that of unstimulated controls, and the amount of type II collagen mRNA as determined by RT-PCR is 6.5-fold greater than that of unstimulated controls.

FIG. 4 is a graphic representation of Northern blot analysis of type II collagen expression (white bar) and type II collagen mRNA expression (shaded bar) when articular cartilage chondrocytes are exposed to 20 mV/cm capacitively coupled electric field for 30 minutes' duration and harvested 5.5 hours after cessation of the electrical signal. As indicated, the Northern blot analysis of the type II collagen mRNA is 3.5-fold greater than that of unstimulated controls, and the amount of type II collagen mRNA as determined by RT-PCR is 6.5-fold greater than that of unstimulated controls.

FIG. 5 is a graphic representation of type II collagen mRNA expression when articular cartilage chondrocytes are exposed to a capacitively coupled electric field of various duty cycles with a duration of 30 minutes ON time at 20 mV/cm electric field amplitude and harvested 5.5 hours after cessation of the electrical signal. As indicated, the optimum duty cycle was found to be 8.3% (1 minute ON, 11 minutes OFF, 30 cycles). By comparison, the optimal duty cycle for aggrecan mRNA expression was found by the present inventor to be 50% (1 minute ON, 1 minute OFF, 30 cycles).

Figure 6:
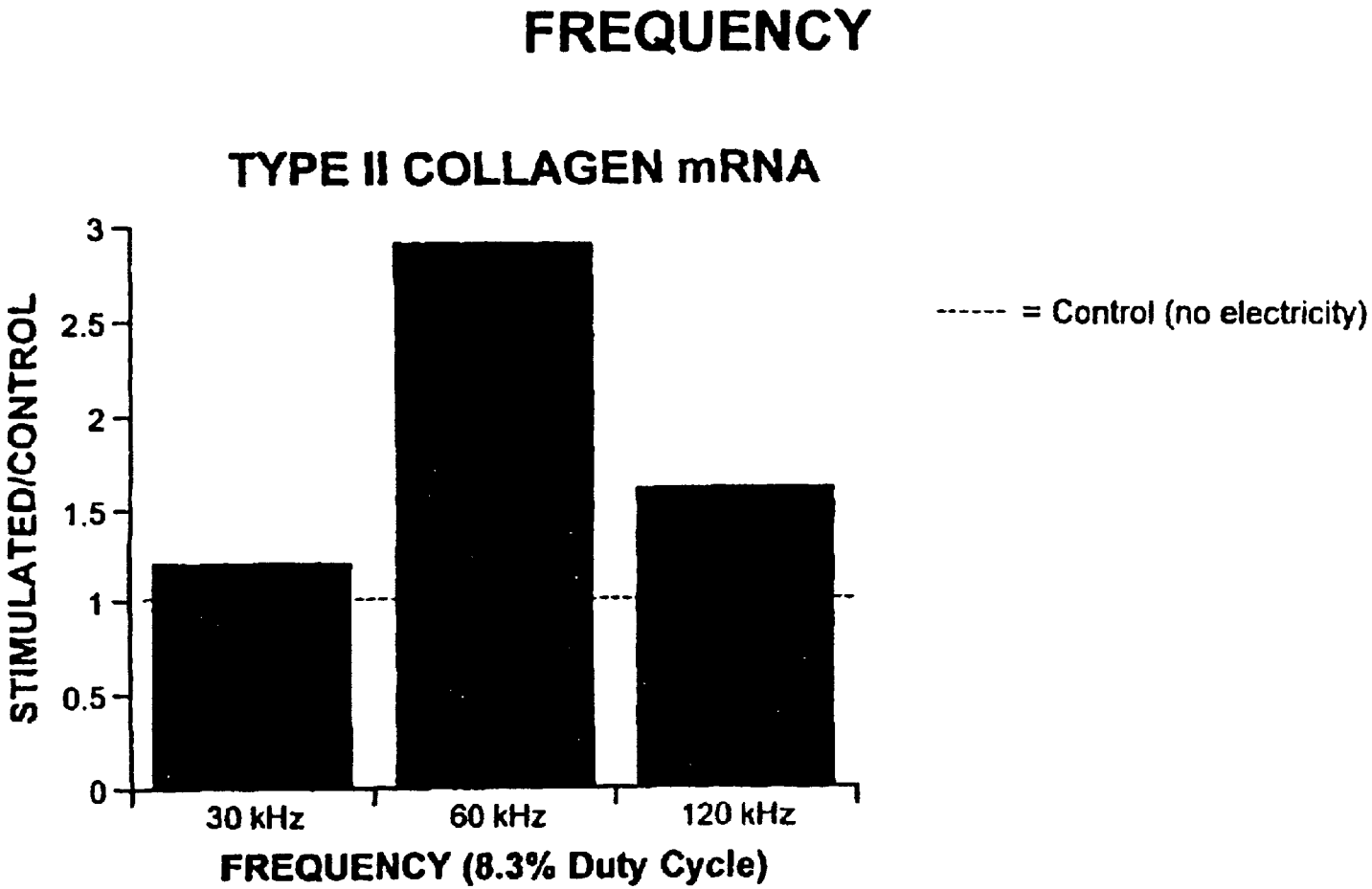
FIG. 6 is a graphic representation of type II collagen mRNA expression when articular cartilage chondrocytes are exposed to a capacitively coupled electric field of various frequencies of 30 minutes' duration (ON time) at 20 mV/cm electric field amplitude with a 8.3% duty cycle (1 minute ON, 11 minutes OFF, 30 cycles) and harvested 5.5 hours after cessation of the electrical signal. As indicated, the optimal frequency was found to be 60 kHz.

FIG. 6 is a graphic representation of type II collagen mRNA expression when articular cartilage chondrocytes are exposed to a capacitively coupled electric field of various frequencies of 30 minutes' duration (ON time) at 20 mV/cm electric field amplitude with a 8.3% duty cycle (1 minute ON, 11 minutes OFF, 30 cycles) and harvested 5.5 hours after cessation of the electrical signal. As indicated, the optimal frequency was found to be 60 kHz.

Figure 7:
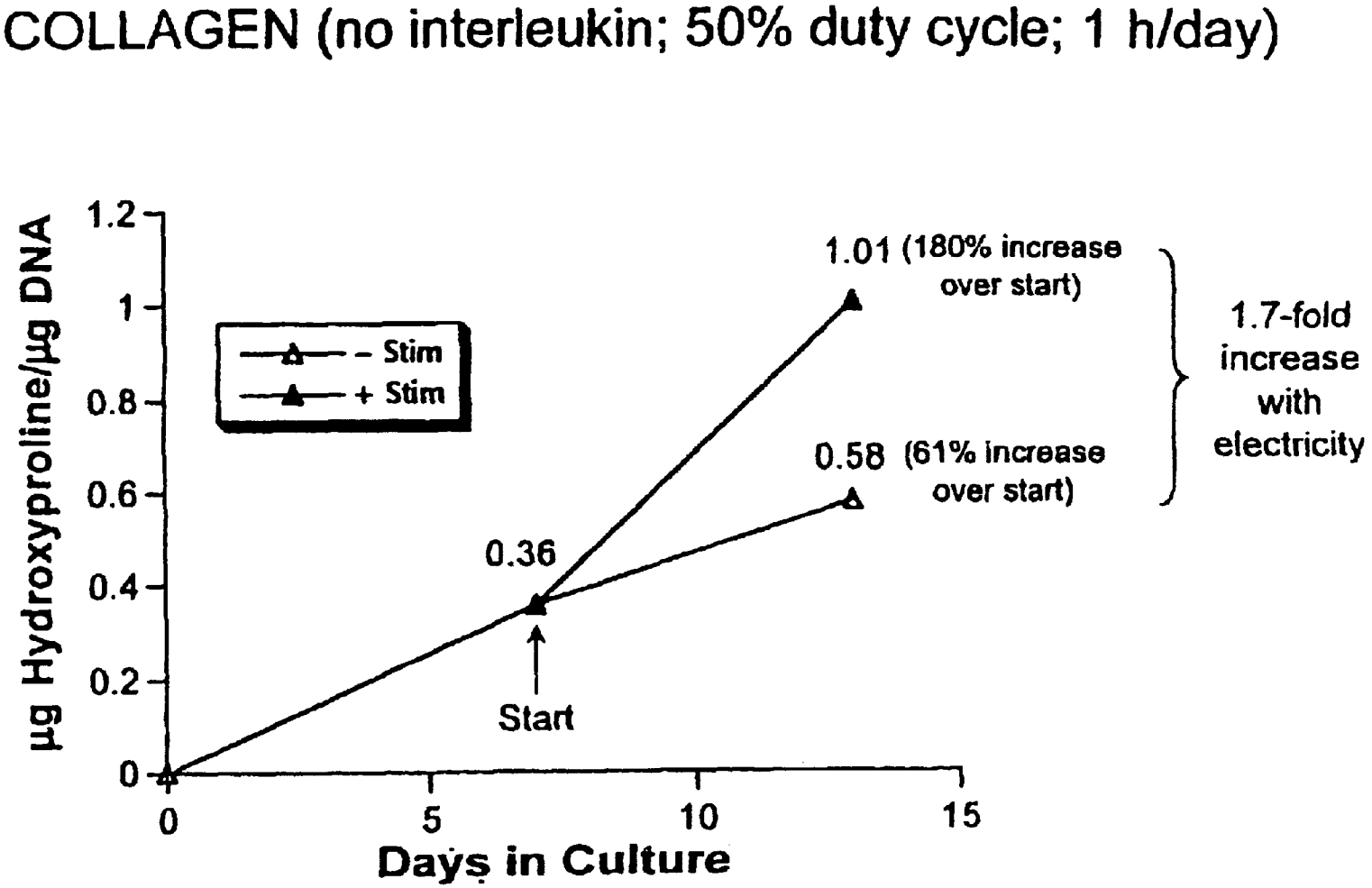
FIG. 7 is a graphic representation of articular cartilage chondrocytes grown for 7 days in culture and then exposed to a capacitively coupled electric field of 20 mV/cm, 50% duty cycle (1 minute ON, 1 minute OFF, 30 cycles), at a frequency of 60 kHz, and having a sine wave configuration. The chondrocytes were exposed to this field for 1 hour per day for 7 days. Control chondrocytes were grown under the same conditions but were not exposed to any electric stimulation. No interleukin-1β (IL-1β), a cytokine that stimulates articular cartilage degradation, was present in the media of these cultures. As indicated, hydroxyproline, an amino acid that is a characteristic constituent of collagen, was increased 1.7-fold when chondrocytes were exposed to the electric field as compared to control chondrocytes that were not exposed to the electric field.

FIG. 7 is a graphic representation of articular cartilage chondrocytes grown for 7 days in culture and then exposed to a capacitively coupled electric field of 20 mV/cm, 50% duty cycle (1 minute ON, 1 minute OFF, 30 cycles), at a frequency of 60 kHz, and having a sine wave configuration. The chondrocytes were exposed to this field for 1 hour per day for 7 days. Control chondrocytes were grown under the same conditions but were not exposed to any electric stimulation. No interleukin-1β (IL-1β), a cytokine that stimulates articular cartilage degradation, was present in the media of these cultures. As indicated, hydroxyproline, an amino acid that is a characteristic constituent of collagen, was increased 1.7-fold when chondrocytes were exposed to the electric field as compared to control chondrocytes that were not exposed to the electric field. Those skilled in the art will appreciate that since the duty cycle used in this experiment (50%) is not the optimal duty cycle for type II collagen (see FIG. 5) an even greater response is expected should the optimal duty cycle (8.3%) be used.

Figure 8:
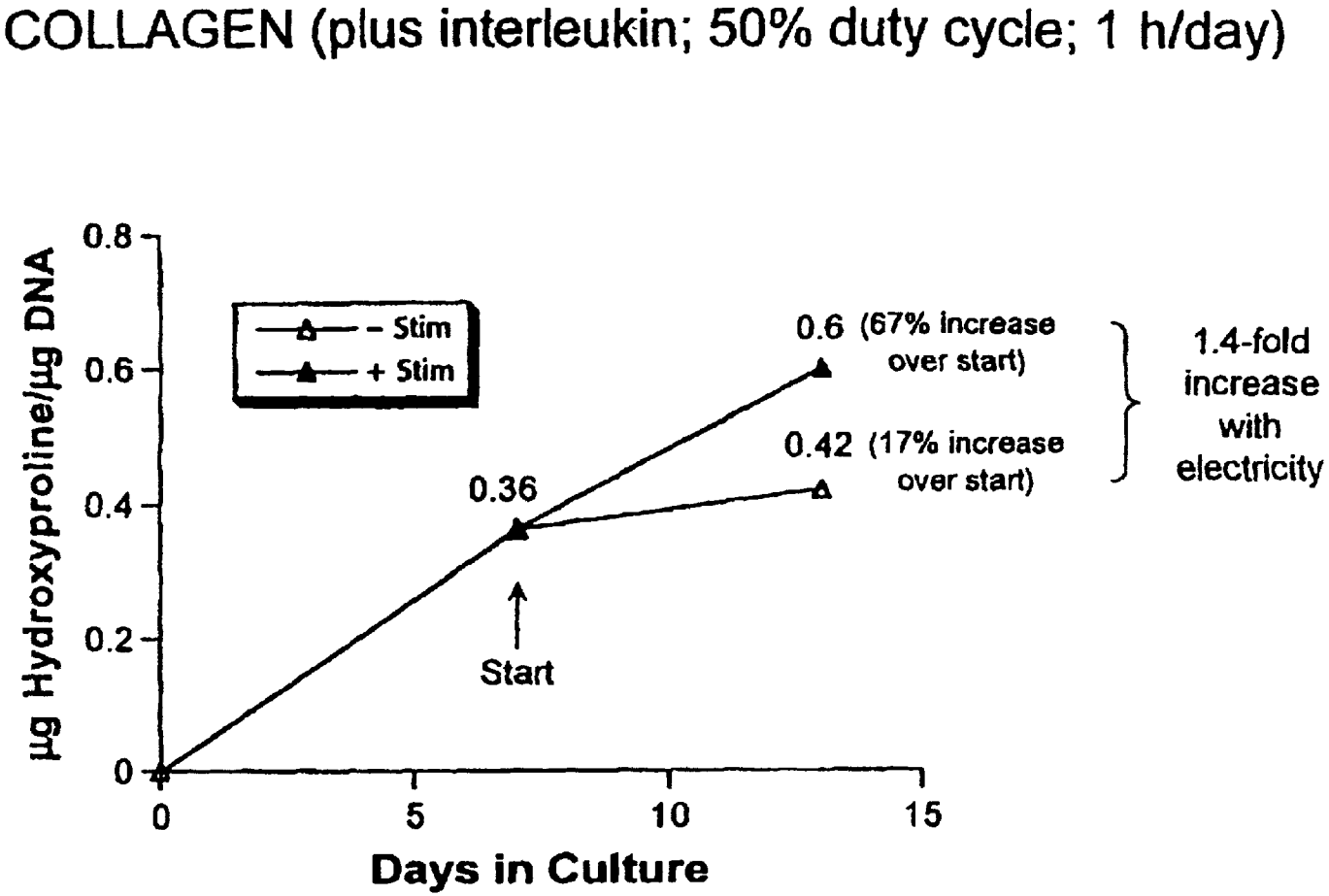
FIG. 8 is a graphic representation of articular cartilage chondrocytes grown for 7 days in culture and then exposed to a capacitively coupled electric field of 20 mV/cm, 50% duty cycle (1 minute ON, 1 minute OFF, 30 cycles), at a frequency of 60 kHz, and having a sine wave configuration. Interleukin-1β (10 ng/ml) was added to the media at day 7. The chondrocytes were then exposed to this field for 1 hour per day for 7 days. Control chondrocytes were grown under the same conditions with interleukin in the media but were not exposed to any electric stimulation. As indicated, hydroxyproline still showed a 1.4-fold increase when exposed to the electric field, despite the presence of interleukin in the media of the cultures, as compared to control cultures that were not exposed to the electric field.

FIG. 8 is a graphic representation of articular cartilage chondrocytes grown for 7 days in culture and then exposed to a capacitively coupled electric field of 20 mV/cm, 50% duty cycle (1 minute ON, 1 minute OFF, 30 cycles), at a frequency of 60 kHz, and having a sine wave configuration. Interleukin-1β (10 ng/ml) was added to the media at day 7. The chondrocytes were then exposed to this field for 1 hour per day for 7 days. Control chondrocytes were grown under the same conditions with interleukin in the media but were not exposed to any electric stimulation. As indicated, hydroxyproline still showed a 1.4-fold increase when exposed to the electric field, despite the presence of interleukin in the media of the cultures, as compared to control cultures that were not exposed to the electric field. Those skilled in the art will appreciate that since the duty cycle used in this experiment (50%) is not the optimal duty cycle for type II collagen (see FIG. 5) an even greater response is expected should the optimal duty cycle (8.3%) be used.

FIG. 9 illustrates a device 10 in accordance with the present invention that is used to treat a patient with osteoarthritis of the knee. As illustrated, two circular, soft conductive, self-adherent electrodes 12 are placed on the skin on either side of the knee at the level of the joint line. The electrodes 12 are attached to a power unit 14 that has a VELCRO® patch 16 on the reverse side such that the power unit 14 can be attached to a VELCRO® strap (not shown) fitted around the calf, thigh or waist. The electrodes 12 may be placed on the skin before the patient goes to bed each evening or any other convenient time. Of course, other suitable types of electrodes 12 may also be used.

The power unit 14 is preferably small (e.g., 6–8 ounces) and powered by a standard 9-volt battery to emit a 5-volt peak-to-peak, 6–10 mAmp, 20 mV/cm, 60 kHz sine wave signal to the electrodes 12 placed on the skin. When this signal is provided approximately 30 minutes per day with the proper duty cycle (8.3%), it has been shown to significantly up-regulate genes encoding type II collagen. This treatment should prevent or minimize further articular cartilage deterioration as well as to heal articular cartilage that already is damaged or degenerated.

The example described above demonstrates that the expression of the type II collagen gene may be significantly up-regulated to increase the production of proteoglycan in articular cartilage so as to treat arthritis (both osteoarthritis and rheumatoid arthritis), cartilage injury, and cartilage defects. Proteoglycan, along with type II collagen, is the main constituent of articular cartilage and is degradated and destroyed early in the development of arthritis. The present invention clearly shows that the optimal electric field described in the example can very significantly up-regulate type II collagen mRNA and, hence, increase proteoglycan synthesis, even in the presence of IL-$\beta_1$. Those skilled in the art will appreciate that an appropriate electric field, as described herein with capacitive coupling, is also equally effective with any and all electromagnetic systems that produce equivalent, or nearly equivalent, electric field characteristics. Those skilled in the art will also appreciate that more particularized signal characteristics may be discovered through more experimentation with more data points, but relatively minor variations in each of the signal characteristics are believed to be within the level of those skilled in the art given the teachings herein.

Those skilled in the art will also appreciate that numerous other modifications to the invention are possible within the scope of the invention. For example, the optimal field described herein can be applied to any joint via two or more appropriate surface electrodes, in pairs or strips, incorporated in garments, braces, wraps, or casts, and delivered by means of capacitive coupling, inductive coupling (electromagnetic fields), or combined fields. Accordingly, the scope of the invention is not intended to be limited to the preferred embodiment described above, but only by the appended claims.

What is claimed is:

1. A method of [specifically and selectively] up-regulating the gene expression of type II collagen mRNA in cartilage tissue, comprising the steps of:

generating at least one specific and selective signal that is selected from possible signals by determining sequential dose response curves for gene expression of type II collagen mRNA in response to respective signal characteristics of said possible signals and selecting a signal from said possible signals that [provides] *has a frequency of about 30 kHz to about 120 kHz and that, when applied to a field generating device operatively disposed with respect to the cartilage tissue causes the generation of* a substantially optimized [dose response curve] *electric field having an amplitude of about 0.2–40 mV/cm in the cartilage tissue* for the up-regulation of the gene expression of type II collagen mRNA when *said field is* applied to the cartilage tissue; and exposing the cartilage tissue to [a specific and selective] *the substantially optimized electric* field generated by [the] *said field generating device upon the application of said at least one* specific and selective signal *thereto* for a predetermined duration of time *of about ½ to about 24 hours per 24 hour period* at *a* predetermined [intervals] *duty cycle from approximately 4.2%–100%* so as to *selectively* up-regulate the gene expression of type II collagen mRNA *in the cartilage tissue*.

2. The method of claim 1 wherein the generating step comprises the step of selectively varying the amplitude, duration, duty cycle, frequency, and/*or* waveform of the specific and selective signal until the magnitudes of the corresponding dose response curves are substantially optimized for up-regulation of the gene expression of type II collagen mRNA in the cartilage tissue by the generated field.

3. The method of claim 1 wherein the exposing step comprises the step of exposing an articular cartilage chrondrocyte to the [specific and selective] *electric* field generated by [the] *said field generating device upon the application of said at least one* specific and selective signal *thereto* for the predetermined duration of time at predetermined intervals of once per day.

4. The method of claim 1 wherein said generating step comprises the step of generating the *at least one* specific and selective signal at a remote source and said exposing step comprises the step of applying *to the cartilage tissue* the [specific and selective] *electric* field generated by [the] *said field generating device upon the application of said at least one* specific and selective signal [to the cartilage tissue] *thereto*.

5. The method of claim 4 wherein the exposing step comprises the step of applying the *at least one* specific and selective signal to *either* electrodes *or at least one coil* located near the cartilage tissue.

6. The method of claim 5 wherein the exposing step comprises the step of applying *to the cartilage tissue* the [specific and selective] *electric* field generated by the *electrodes or at least one coil as a result of application of said at least one* specific and selective signal to the cartilage tissue through [one of] *either* capacitive coupling [and] *or* inductive coupling.

7. The method of claim 6 wherein the *at least one* specific and selective signal *when applied to electrodes* causes the electrodes to generate [one of] a capacitive coupling electric field, *and when applied to the coil(s) causes the coil(s) to generate* an electromagnetic field[, and] *or* a combined field.

8. A method for treating [at least one of] osteoarthritis, rheumatoid arthritis, cartilage injury, and/*or* cartilage defects, comprising the steps of:

generating at least one specific and selective signal *having a frequency from about 30 kHz to about 120 kHz* that [up-regulates] *when applied to a field generating device operatively disposed with respect to target cartilage tissue causes the generation of an electric field having an amplitude of about 0.2–4.0 mV/cm in the target cartilage tissue that is specific and selective for up-regulating* the gene expression of type II collagen mRNA *when said electric field is applied to the target cartilage tissue*; and exposing *the* cartilage tissue to [a specific and selective] *the electric* field generated by [the] *said field generating device upon the application of said at least one* specific and selective signal *thereto* for a predetermined duration *of time of about ½ to about 24 hours per 24 hour period* at *a* predetermined [intervals] *duty cycle from approximately 4.2%–100%* so as to selectively up-regulate gene expression of type II collagen mRNA *in the target cartilage tissue*.

9. The method of claim 8 wherein the exposing step comprises the step of capacitively coupling the [specific and selective] *electric* field to the *target* cartilage tissue.

10. The method of claim 8 wherein the exposing step comprises the step of applying [one of] *either* an electromagnetic field [and] *or* a combined field *generated by one or more coils* to the *target* cartilage tissue.

11. The method of claim 8 wherein the generating step comprises the step of generating [a specific and selective] *an* electric field having an amplitude of approximately 20 mV/cm[,] *in the target cartilage tissue from a specific and selective signal having* a sine wave configuration, a duty cycle of approximately 1/12, and a frequency of approximately 60 kHz.

12. The method of claim 11 wherein the exposing step comprises the step of applying the [specific and selective] electric field to the *target* cartilage tissue for a duration of approximately 30 minutes every 24 hours.

13. The method of claim 8 wherein the generating step comprises the steps of selectively varying the amplitude, duration, duty cycle, frequency, and/*or* waveform of the specific and selective signal until the magnitudes of the corresponding dose response curves are substantially optimized for up-regulation of the gene expression of type II collagen mRNA in the *target* cartilage tissue by the generated field.

14. The method of claim 13 wherein the exposing step comprises the step of applying the [specific and selective] *electric* field generated by *said field generating device, upon the application of* the specific and selective signal *thereto,* to the *target* cartilage tissue through [one of] *either* capacitive coupling [and] *or* inductive coupling.

15. The method of claim 14 wherein *application of* the specific and selective signal *to said field generating device* causes the [electrodes to generate one] *generation* of a capacitive coupling electric field, an electromagnetic field, [and] *or* a combined field.

16. A method [of] *for* treating [at least one of] osteoarthritis, rheumatoid arthritis, cartilage injury, and/*or* a cartilage defect comprising the steps of:

exposing cartilage tissue to the specific and selective field generated by a device comprising a signal source that provides at least one *specific and selective* signal [that creates a field] *and a field generating device connected to the signal source so as to receive said at least one specific and selective signal and that is operatively disposed with respect to target cartilage tissue, said field generating device upon receipt of said at least one* specific and selective *signal causing the generation of an electric field that is specific and selective* for up-regulating gene expression of type II collagen mRNA *in said target cartilage tissue*, the specific and selective signal having a sine wave configuration *and approximately a 1/12 duty cycle* and [generating a] *said* specific and selective electric field having an amplitude of about 20 mV/cm at 60 kHz [with approximately a 1/12 duty cycle, and electrodes connected to the signal source that receive], said [at least one] specific and selective [signal for application of the] field *being applied* to the cartilage tissue via [one of] *either* capacitive coupling [and] *or* inductive coupling; and selectively up-regulating gene expression of type II collagen mRNA in the *target* cartilage tissue for a predetermined duration at predetermined intervals using said device.

17. The method of claim 1 wherein the generating step comprises the step of generating [a specific and selective] *an* electric field having an amplitude of approximately 20 mV/cm[.] *in the target cartilage tissue from a specific and selective signal having* a sine wave configuration, a duty cycle of approximately 1/12, and a frequency of approximately 60 kHz.

18. The method of claim 17 wherein the exposing step comprises the step of applying the [specific and selective] electric field to the *target* cartilage tissue for a duration of approximately 30 minutes every 24 hours.

*19. A method of up-regulating the gene expression of type II collagen mRNA in cartilage tissue, comprising the steps of:*

*generating at least one specific and selective signal having a frequency of about 30 kHz to about 120 kHz that when applied to a field generating device operatively disposed with respect to the cartilage tissue causes the generation of an electric field having an amplitude of about 0.2–40 mV/cm in the cartilage tissue that is specific and selective for the up-regulation of the gene expression of type II collagen mRNA when said electric field is applied to the cartilage tissue containing said type II collagen mRNA; and*

*exposing the cartilage tissue to the specific and selective electric field generated by said field generating device upon the application of said at least one specific and selective signal thereto for a predetermined duration of time of about 1/2 to about 24 hours per 24 hour period at a predetermined duty cycle from approximately 4.2%–100% so as to selectively up-regulate the gene expression of type II collagen mRNA in the cartilage tissue.*

*20. The method of claim 19 wherein the generating step comprises the step of selectively varying the amplitude, duration, duty cycle, frequency, and/or waveform of the specific and selective signal until the up-regulation of type II collagen mRNA in the cartilage tissue in response to the specific and selective electric field resulting from application of the specific and selective signal to said field generating device is substantially optimized.*

*21. The method of claim 19 wherein the exposing step comprises the step of exposing an articular cartilage chrondrocyte to the electric field generated by said field generating device upon the application of said at least one specific and selective signal thereto for the predetermined duration of time at predetermined intervals of once per day.*

*22. The method of claim 19 wherein said generating step comprises the step of generating the at least one specific and selective signal at a remote source and said exposing step comprises the step of applying to the cartilage tissue the electric field generated by said field generating device upon the application of said at least one specific and selective signal thereto.*

*23. The method of claim 22 wherein the exposing step comprises the step of applying the at least one specific and selective signal to either electrodes or at least one coil located near the cartilage tissue.*

*24. The method of claim 23 wherein the exposing step comprises the step of applying to the cartilage tissue the electric field generated by the electrodes or at least one coil as a result of application of said at least one specific and selective signal thereto through either capacitive coupling or inductive coupling.*

*25. The method of claim 24 wherein the at least one specific and selective signal when applied to electrodes causes the electrodes to generate a capacitive coupling electric field, and when applied to the coil(s) causes the coil(s) to generate an electromagnetic field or a combined field.*

* * * * *

UNITED STATES PATENT AND TRADEMARK OFFICE

CERTIFICATE OF CORRECTION

PATENT NO. : RE41,391 E
APPLICATION NO. : 11/880422
DATED : June 22, 2010
INVENTOR(S) : Carl T. Brighton It is certified that error appears in the above-identified patent and that said Letters Patent is hereby corrected as shown below:

In the Claims

Column 14,
Line 25, Claim 8, delete "*0.2–4.0 mV/cm*" and insert -- *0.2–40 mV/cm* --.

Signed and Sealed this
Eighth Day of April, 2014

Michelle K. Lee

Michelle K. Lee
*Deputy Director of the United States Patent and Trademark Office*